United States Patent [19]

Ueda et al.

[11] Patent Number: 4,916,138
[45] Date of Patent: Apr. 10, 1990

[54] SOLID DISPERSION COMPOSITION OF FR-900506 SUBSTANCE

[75] Inventors: Yoshio Ueda, Kobe; Fumio Shimojo, Kawanishi; Yasuo Shimazaki, Takarazuka; Kazutake Kado, Ikeda; Toshiyasu Honbo, Kobe, all of Japan

[73] Assignee: Fujisawa Pharmaceutical Co., Ltd., Osaka, Japan

[21] Appl. No.: 224,235

[22] Filed: Jul. 25, 1988

Related U.S. Application Data

[63] Continuation of Ser. No. 32,572, Apr. 1, 1987, abandoned.

[30] Foreign Application Priority Data

Apr. 2, 1986 [GB] United Kingdom ................ 8608080

[51] Int. Cl.$^4$ .............................................. A61K 31/44
[52] U.S. Cl. .................................................... 514/294
[58] Field of Search ........................ 514/294; 374/294

[56] References Cited

U.S. PATENT DOCUMENTS

| | | |
|---|---|---|
| 3,852,421 | 12/1974 | Koyanagi et al. |
| 4,259,314 | 3/1981 | Lowey |
| 4,265,875 | 5/1981 | Byrne et al. |
| 4,369,172 | 1/1983 | Schor et al. |
| 4,389,393 | 6/1983 | Schor et al. |
| 4,412,986 | 11/1983 | Kawata et al. |
| 4,654,206 | 3/1987 | Okuda et al. |

FOREIGN PATENT DOCUMENTS

| | | |
|---|---|---|
| 0184162 | 6/1986 | European Pat. Off. ............ 514/294 |
| 852904 | 4/1986 | Greece . |
| 2050828 | 1/1981 | United Kingdom . |
| 2053681 | 2/1981 | United Kingdom . |
| 2111386 | 7/1983 | United Kingdom . |
| 2122085 | 1/1984 | United Kingdom . |

OTHER PUBLICATIONS

Pharmaceutica 1981, No. 4, pp. 66–67, Reviews, Tentsova et al, "Solid Disperse Systems in Pharmaceutics".

*Primary Examiner*—Jerome D. Goldberg
*Attorney, Agent, or Firm*—Oblon, Spivak, McClelland, Maier & Neustadt

[57] ABSTRACT

This invention relates to a solid dispersion composition comprising FR-900506 substance and water-soluble hydroxypropyl methylcellulose which is capable of dispersing the FR-900506 substance, the FR-900506 substance and hydroxypropyl methylcellulose being in the ratio of 1:0.1 to 1:20 by weight.

3 Claims, No Drawings

SOLID DISPERSION COMPOSITION OF FR-900506 SUBSTANCE

This application is a continuation of application Ser. No. 32,572, filed on Apr. 1, 1987, now abandoned.

The present invention relates to a solid dispersion composition comprising 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (hereinafter referred to as FR-900506 substance).

More particularly, the present invention relates to a solid dispersion composition comprising the FR-900506 substance and a water-soluble polymer.

The FR-900506 substance used in the present invention is novel and can be represented by the following chemical formula:

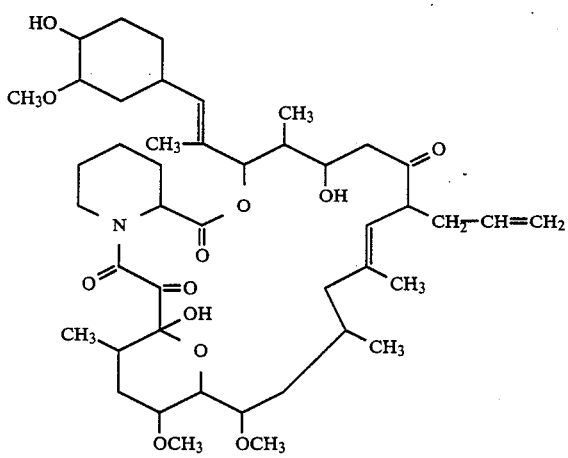

The FR-900506 substance was isolated in a pure form from culture broths prepared by fermentation of a FR-900506 substance-producing strain belonging to genus Streptomyces, among which *Streptomyces tsukubaensis* No. 9993 has been newly isolated from a soil sample collected at Toyosato-cho, Tsukuba-gun, Ibaraki Prefecture, Japan. And a lyophilized sample of the newly isolated *Streptomyces tsukubaensis* No. 9993 has been deposited with the Fermentation Research Institute, Agency of Industrial Science and Technology (No. 1-3, Higashi 1-chome, Yatabemachi, Tsukuba-gun, Ibaraki Prefecture, Japan) under the deposit number of FERM P-7886 (deposited date: Oct. 5th, 1984), and then converted to Budapest Treaty route of the same depository on Oct. 19, 1985 under the new deposit number of FERM BP-927.

The FR-900506 substance possesses pharmacological activities such as immunosuppressive activity and anti-microbial activity as described in the published European patent publication No. 184162 (publication date: June 11, 1986) and therefore is useful for treatment and prevention of rejection by transplantation, graft-versus-host diseases by medulla ossium transplantation, auto-immune diseases, infectious diseases, and the like.

However, when orally administered, the ratio of the absorption of the FR-900506 substance into blood is insufficient due to its insolubility into water, and the FR-900506 substance has the disadvantage of its poor bioavailability in oral administration.

As a result of an extensive study, the inventors of the present invention have discovered the fact that said disadvantage could be overcome by dispersing the FR-900506 substance with a water-soluble polymer to prepare a solid dispersion composition, and have completed the present invention.

According to the solid dispersion composition of the present invention, solubilization of the FR-900506 substance has been achieved and hence the bioavailability of the FR-900506 substance in human body can be drastically improved.

Further, according to the present invention, the FR-900506 substance become stable and can be released sustainedly, and therefore said substance can be pharmacologically active for a long time in the body and its toxicity can be reduced thereby.

The solid dispersion composition of the present invention is explained in more detail in the following.

The solid dispersion composition of the FR-900506 substance can be prepared by a conventional method, for example;

(1) dissolving the FR-900506 substance in an organic solvent, and (2) adding a water-soluble polymer to the resultant solution, and (3) if necessary, suspending the additives such as excipient, disintergator, and the like, in the resultant suspension or solution, and then (4) removing the organic solvent from the resultant homogeneous suspension in a conventional manner.

And, in case that more homogeneous solid dispersion composition is desired, the homogeneous suspension is prepared in the above procedure (2) and then subjected to the following subsequent procedures.

(5) dissolving the suspension prepared in the above procedure (2) in an organic solvent, and (6) if necessary, suspending the additives such as excipient, disintegrator, and the like, in the resultant homogeneous solution, and then (7) removing the organic solvent in a conventional manner.

The organic solvents to be used in the procedure (1) are not restrictive and are any solvents which are capable of dissolving the FR-900506 substance such as alcohol (e.g. methanol, ethanol, propanol, isopropyl alcohol, etc.), ethyl acetate, diethyl ether, and the like, in which the preferable ones may be lower alkanol.

The water-soluble polymers to be used in the procedure (2) may be a water-soluble cellulose polymer which is capable of dispersing the FR-900506 substance, such as hydroxypropyl methylcellulose. The hydroxypropyl methylcellulose can be used under various viscosity.

The quantity of the water-soluble polymer is not restrictive and is any one, by which the FR-900506 substance can be dispersed, and suitable quantitative ratio of the water-soluble polymer and the FR-900506 substance by weight may be from 0.1:1 to 20:1, preferably 0.3:1 to 10:1, more preferably 0.5:1 to 5:1, and the most preferably 1:1.

The additives to be optionally used in the procedures (3) and (6) may be a conventional ones used in the field of pharmaceutical preparation such as excipient (e.g. lactose, sucrose, starch, mannitol, etc.), disintegrator (e.g. croscarmellose sodium, carboxymethyl cellulose calcium, low substituted hydroxypropyl cellulose, sodium starch glycolate, microcrystalline cellulose, etc.), and the like, and these excipient and disintegrator can be used at the same time or independently.

The quantity of the additives is not restrictive and suitable quantitative ratio of the excipient or disintegrator and the FR-900506 substance by weight, if used, may be from 0.1:1 to 20:1, preferably 0.5:1 to 5:1, and more preferably 1:1 to 3:1, respectively.

The organic solvents to be used in the procedure (5) are not restrictive and are any solvents capable of dissolving the suspension of the preceding procedure (2), such as chloroform, dichloromethane, and the like.

The solid dispersion composition of the present invention prepared by the above-mentioned procedures can be used by itself as a pharmaceutical preparation for oral administration and also can be converted into various dosage forms such as powders, fine granules, granules, tablets, capsules, injection, and the like, according to a conventional manner. If desired, conventional coloring agents, sweeting agents, flavouring agents, diluents, lubricants, and the like, (e.g. sucrose, lactose, starch, crystalline cellulose, synthetic aluminum silicate, magnesium stearate, talc, etc.) may be compounded with the solid dispersion composition.

The solid dispersion composition of the FR-900506 substance and the various preparations thereof prepared by optionally converting said solid dispersion composition into various dosage forms as mentioned above, have remarkably improved solubility and absorptiveness into blood in comparison to the crystals of the FR-900506 substance per se.

In order to show the usefulness of the solid dispersion composition of the present invention, the test results are given in the following.

[I] Dissolution Test:

Test Samples (A) Solid dispersion composition of the FR No. 900506 substance prepared in Example 2;
(B) Solid dispersion composition of the FR No. 900506 substance prepared in Example 4;
(C) Crystals of the FR No. 900506 substance per se prepared in Reference;

Test Method

The tests were carried out according to the paddle method prescribed in Method 2 of the dissolution test in The Pharmacopoeia of Japan (tenth edition) using water as test solution and the dissolution rate at 100 rpm after the specified minutes from the beginning of each dissolution test was measured.

Test Results

The dissolution rate of the solid dispersion composition of the FR No. 900506 substance is shown in the following table.

| Test Samples | Dissolution Rate (%) | | | |
| --- | --- | --- | --- | --- |
| | 15 min. | 30 min. | 60 min. | 90 min. |
| A | 54.5 | 74.6 | 88.2 | 93.0 |
| B | 74.0 | 91.8 | 100 | 100 |
| C | 0 | 0 | 5.0 | 10.8 |

[II] Bioavailability Test

Test Sample

Solid dispersion composition of the FR No. 900506 substance prepared in Example 2;

Test Method

The above sample, which contains 10 mg/kg of the FR No. 900506 substance, was orally administered to several dogs, which had been withheld from any food overnight in a crossover design. The plasma concentration of the FR No. 900506 substance was determined by high performance liquid chromatography at 1, 2, 4 and 6 hours after administration.

Test Results

The plasma concentrations of the FR No. 900506 substance at each time are shown in the following table.

| Time (hours) | Plasma Concentrations ($\mu$g/ml) |
| --- | --- |
| 1 | 0.44 |
| 2 | 0.69 |
| 4 | 0.53 |
| 6 | 0.45 |

As clearly seen from the above two test results, the solid dispersion composition of the present invention possesses good dissolution rate and pattern, and further good bioavailability.

The present invention is explained according to the following Examples.

Reference

Isolation of *Streptomyces tsukubaensis* No. 9993

*Streptomyces tsukubaensis* No. 9993 was isolated by using dilution plate techniques as shown in the following.

About one gram soil which was collected at Toyosato-cho, Tsukuba-gun, Ibaraki Prefecture, Japan, was added to a sterile test tube and the volume made up to 5 ml with sterile water. The mixture was then blended for 10 second by a tube buzzer and kept on 10 minutes. The supernatant was sequentially diluted by 100 fold with sterile water. The diluted solution (0.1 ml) was spread on Czapek agar supplemented with thiamine hydrochloride (saccharose 30 g, sodium nitrate 3 g, dipotassium phosphate 1 g, magnesium sulfate 0.5 g, potassium chloride 0.5 g, ferrous sulfate 0.01 g, thiamine hydrochloride 0.1 g, agar 20 g, tap water 1000 ml; pH 7.2) in a Petri dish. The growing colonies developed on the plates after 21 days incubation at 30° C. were transferred to slants [yeast-malt extract agar (ISP-medium 2)], and cultured for 10 days at 30° C. Among of the colonies isolated, the *Streptomyces tsukubaensis* No. 9993 could be found.

Fermentation

A preculture medium (100 ml) containing glycerin (1%), corn starch (1%), glucose (0.5%), cottonseed meal (1%), corn steep liquor (0.5%), dried yeast (0.5%) and calcium carbonate (0.2%) at pH 6.5 was poured into a 500 ml-Erlenmeyer flask and sterilized at 120° C. for 30 minutes. A loopful of slant culture of *Streptomyces tsukubaensis* No. 9993 was inoculated to the medium and cultured at 30° C. for four days. The resultant culture was transferred to the same preculture medium (20 liters) in 30 liters jar-fermentor which had been sterilized at 120° C. for 30 minutes in advance. After the culture was incubated at 30° C. for 2 days, 16 liters of the preculture was inoculated to a fermentation medium (1600 liters) containing soluble starch (4.5%), corn steep liquor (1%), dried yeast (1%), calcium carbonate (0.1%) and Adekanol (defoaming agent, Trade Mark, maker Asahi Denka Co.) (0.1%) at pH 6.8 in 2 ton tank which had been sterilized at 120° C. for 30 minutes in advance and cultured at 30° C. for 4 days.

Isolation and Purification

The cultured broth thus obtained was filtered with an aid of diatomaseous earth (25 kg). The mycelial cake was extracted with acetone (500 liters), yielding 500 liters of the extract. The acetone extract from mycelium and the filtrate (1350 liters) were combined and passed through a column of a non-ionic adsorption resin "Diaion HP-20" (Trade Mark, maker Mitsubishi Chemical Industries Ltd.) (100 liters). After washing with water (300 liters) and 50% aqueous acetone (300 liters), elution was carried out with 75% aqueous acetone. The eluate was evaporated under reduced pressure to give residual water (300 liters). This residue was extracted with ethyl acetate (20 liters) three times. The ethyl acetate extract was concentrated under reduced pressure to give an oily residue. The oily residue was mixed with twice weight of acidic silica gel (special silica gel grade 12, maker Fuji Devison Co.), and this mixture was slurried in ethyl acetate. After evaporating the solvent, the resultant dry powder was subjected to column chromatography of the same acidic silica gel (8 liters) which was packed with n-hexane. The column was developed with n-hexane (30 liters), a mixture of n-hexane and ethyl acetate (4:1 v/v, 30 liters) and ethyl acetate (30 liters). The fractions containing the object compound were collected and concentrated under reduced pressure to give an oily residue. The oily residue was mixed with twice weight of acidic silica gel and this mixture was slurried in ethyl acetate. After evaporating the solvent, the resultant dry powder was rechromatographed on acidic silica gel (3.5 liters) packed with n-hexane. The column was developed with n-hexane (10 liters), a mixture of n-hexane and ethyl acetate (4:1 v/v, 10 liters) and ethyl acetate (10 liters). Fractions containing the object compound were collected and concentrated under reduced pressure to give a yellowish oil. The oily residue was dissolved in a mixture of n-hexane and ethyl acetate (1:1 v/v, 300 ml) and subjected to column chromatography of silica gel (maker Merck Co., Ltd. 230–400 mesh) (2 liters) packed with the same solvents system. Elution was curried out with a mixture of n-hexane and ethyl acetate (1:1 v/v, 10 liters and 1:2 v/v 6 liters) and ethyl acetate (6 liters).

Fractions containing the first object compound were collected and concentrated under reduced pressure to give FR No. 900506 substance in the form of white powder (34 g). This white powder was dissolved in acetonitrile and concentrated under reduced pressure. This concentrate was kept at 5° C. overnight and prisms (22.7 g) were obtained. Recrystallization from the same solvent gave purified FR No. 900506 substance (13.6 g) as colorless prisms.

Infrared Absorption Spectrum: $\nu_{max}^{CHCl_3}$: 3680, 3580, 3520, 2930, 2870, 2830, 1745, 1720, 1700, 1645, 1450, 1380, 1350, 1330, 1310, 1285, 1170, 1135, 1090, 1050, 1030, 1000, 990, 960(sh), 918 cm$^{-1}$

EXAMPLE 1

| | |
|---|---|
| FR-900506 substance | 1 g |
| Hydroxypropyl methylcellulose 2910 (TC-5R) | 1 g |
| Lactose | 3 g |
| Total | 5 g |

The FR No. 900506 substance (1 g) was dissolved in ethanol (10 ml), and thereto was added hydroxypropyl methylcellulose 2910 (Trade Mark: TC-5R, Maker: Shin-Etsu Chemical Co., Ltd.) (1 g) to prepare a suspension. To this suspension was added dichloromethane (5 ml) to prepare a homogeneous solution. Lactose (3 g) was homogeneously suspended to this solution and then the organic solvent was removed by evaporation. The residual product was dried under reduced pressure for 10 hours by vacuum dryer, milled for 2 minutes by coffee mill and then passed through a sieve (32 mesh) to give the above-identified solid dispersion composition of the FR No. 900506 substance (5 g).

EXAMPLE 2

| | |
|---|---|
| FR-900506 substance | 1 g |
| Hydroxypropyl methylcellulose 2910 (TC-5R) | 1 g |
| Lactose | 2 g |
| Croscarmellose sodium (Ac-Di-Sol) | 1 g |
| Total | 5 g |

The FR No. 900506 substance (1 g) was dissolved in ethanol (10 ml), and thereto was added hydroxypropyl methylcellulose 2910 (TC-5R) (1 g) to prepare a suspension. To this suspension was added dichloromethane (5 ml) to prepare a homogeneous solution. Lactose (2 g) and croscarmellose sodium (Trade Mark: Ac-Di-Sol, Maker: Asahi Chemical Industry Co., Ltd.) were homogeneously suspended to this solution and then the organic solvent was removed by evaporation. The residual product was dried under reduced pressure for 10 hours by vacuum dryer, milled for 2 minutes by coffee mill and then passed through a sieve (32 mesh) to give the above-identified solid dispersion composition of the FR-900506 substance (5 g).

EXAMPLE 3

| | |
|---|---|
| FR-900506 substance | 1 g |
| Hydroxypropyl methylcellulose 2910 (TC-5R) | 1 g |
| Lactose | 1 g |
| Croscarmellose sodium (Ac-Di-Sol) | 2 g |
| Total | 5 g |

The above-identified solid dispersion composition of the FR-900506 substance (5 g) was obtained in substantially the same manner to that of Example 2.

EXAMPLE 4

| | |
|---|---|
| FR-900506 substance | 1 g |
| Hydroxypropyl methylcellulose 2910 (TC-5R) | 1 g |
| Croscarmellose sodium (Ac-Di-Sol) | 3 g |
| Total | 5 g |

The FR-900506 substance (1 g) was dissolved in ethanol (10 ml), and thereto was added hydroxypropyl methylcellulose 2910 (TC-5R) (1 g) to prepare a suspension. To this suspension was added dichloromethane (5 ml) to prepare a homogeneous solution. Croscarmellose sodium (Ac-Di-Sol) (3 g) was homogeneously suspended to this solution and then the organic solvent was removed by evaporation. The residual product was dried under reduced pressure for 10 hours by vacuum dryer, milled for 2 minutes by coffee mill and then passed through a sieve (32 mesh) to give a solid dispersion composition of the FR-900506 substance (5 g).

EXAMPLE 5

FR-900506 substance
Hydroxypropyl methylcellulose 2910 (TC-5R)

The solid dispersion compositions comprising various ratio of the above two ingredients were obtained by the following method.

[Method]

The FR-900506 substance (1 g) was dissolved in ethanol (10 ml), and thereto was added hydroxypropyl methylcellulose 2910 (TC-5R) (each 0.5 g, 1 g, 3 g or 5 g) to prepare a suspension. To this suspension was added dichloromethane (5 ml) to prepare a homogeneous solution. The organic solvent was removed from the solution by evaporation, and the residue was dried under reduced pressure for 10 hours by vacuum dryer, milled for 2 minutes by coffee mill and passed through a sieve (32 mesh) to give the above-identified solid dispersion composition in the following ratio.

The ratio of the FR-900506 substance: hydroxypropyl methylcellulose 2910 by weight are 1:0.5, 1:1, 1:3 and 1:5.

EXAMPLE 6

| | |
|---|---|
| FR-900506 substance | 1 g |
| Hydroxypropyl methylcellulose 2910 (TC-5R) | 1 g |
| Total | 2 g |

The FR-900506 substance (1 g) was dissolved in ethanol (10 ml), and thereto was added hydroxypropyl methylcellulose 2910 (TC-5R) (1 g) to prepare a suspension. The organic solvent was removed by evaporation from the suspension, and the residue was dried under reduced pressure for 10 hours by vacuum dryer, milled for 2 minutes by coffee mill and then passed through a sieve (32 mesh) to give the above-identified solid dispersion composition of the FR-900506 substance (2 g).

What we claim is:

1. A solid dispersion composition comprising FR-900506 substance and water-soluble hydroxypropyl methylcellulose which is capable of dispersing the FR-900506 substance, the FR-900506 substance and hydroxypropyl methylcellulose being in the ratio of 1:0.1 to 1:20 by weight.

2. The solid dispersion composition of claim 1, in which the FR-900506 substance and hydroxypropyl methylcellulose are in the ratio of 1:0.5 to 1:5 by weight.

3. The solid dispersion composition of claim 2, in which the FR-900506 substance and hydroxypropyl methylcellulose are in the ratio of 1:1 by weight.

* * * * *